(12) United States Patent
Kaneda et al.

(10) Patent No.: US 12,110,296 B2
(45) Date of Patent: Oct. 8, 2024

(54) COMPOUND, AND METHOD FOR PRODUCING THE SAME

(71) Applicants: N.E. CHEMCAT CORPORATION, Minato-ku (JP); OSAKA UNIVERSITY, Suita (JP)

(72) Inventors: Kiyotomi Kaneda, Suita (JP); Takato Mitsudome, Suita (JP); Yoshiyuki Wada, Minato-ku (JP); Yukio Takagi, Minato-ku (JP)

(73) Assignees: N.E. CHEMCAT CORPORATION, Minato-ku (JP); OSAKA UNIVERSITY, Suita (JP)

( * ) Notice: Subject to any disclaimer, the term of this patent is extended or adjusted under 35 U.S.C. 154(b) by 843 days.

(21) Appl. No.: 17/283,385

(22) PCT Filed: Oct. 7, 2019

(86) PCT No.: PCT/JP2019/039501
§ 371 (c)(1),
(2) Date: Apr. 7, 2021

(87) PCT Pub. No.: WO2020/080165
PCT Pub. Date: Apr. 23, 2020

(65) Prior Publication Data
US 2021/0380594 A1 Dec. 9, 2021

(30) Foreign Application Priority Data
Oct. 17, 2018 (JP) .................. 2018-196008

(51) Int. Cl.
| | | |
|---|---|---|
| C07D 487/08 | (2006.01) | |
| B01J 6/00 | (2006.01) | |
| B01J 23/648 | (2006.01) | |
| B01J 23/652 | (2006.01) | |
| B01J 27/18 | (2006.01) | |
| B01J 37/00 | (2006.01) | |
| B01J 37/04 | (2006.01) | |

(52) U.S. Cl.
CPC ............ *C07D 487/08* (2013.01); *B01J 6/001* (2013.01); *B01J 23/6482* (2013.01); *B01J 23/6525* (2013.01); *B01J 27/1806* (2013.01); *B01J 37/0036* (2013.01); *B01J 37/04* (2013.01)

(58) Field of Classification Search
CPC .................................................... C07D 487/08
See application file for complete search history.

(56) References Cited

U.S. PATENT DOCUMENTS

| | | |
|---|---|---|
| 6,049,018 A | 4/2000 | Calabro et al. |
| 6,656,268 B2 | 12/2003 | Dhingra et al. |
| 2002/0174824 A1 | 11/2002 | Dhingra et al. |

FOREIGN PATENT DOCUMENTS

| | | |
|---|---|---|
| EP | 1 194 375 A | 4/2002 |
| JP | 5-333469 A | 12/1993 |
| JP | 2016-169139 A | 9/2016 |

OTHER PUBLICATIONS

International Search Report issued Nov. 26, 2019 in PCT/JP2019/039501 filed Oct. 7, 2019, citing document AC therein, 2 pages.

*Primary Examiner* — Laura L Stockton
(74) *Attorney, Agent, or Firm* — Oblon, McClelland, Maier & Neustadt, L.L.P.

(57) ABSTRACT

The present invention provides a method for producing a compound represented by formula (2), comprising at least a step of preparing a compound represented by formula (1) and a step of reacting the compound represented by formula (1) with a hydrogen source using a catalyst,

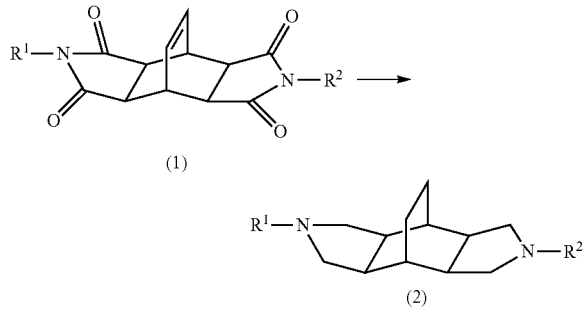

wherein $R^1$ and $R^2$ are each independently an alkyl group.

7 Claims, 1 Drawing Sheet

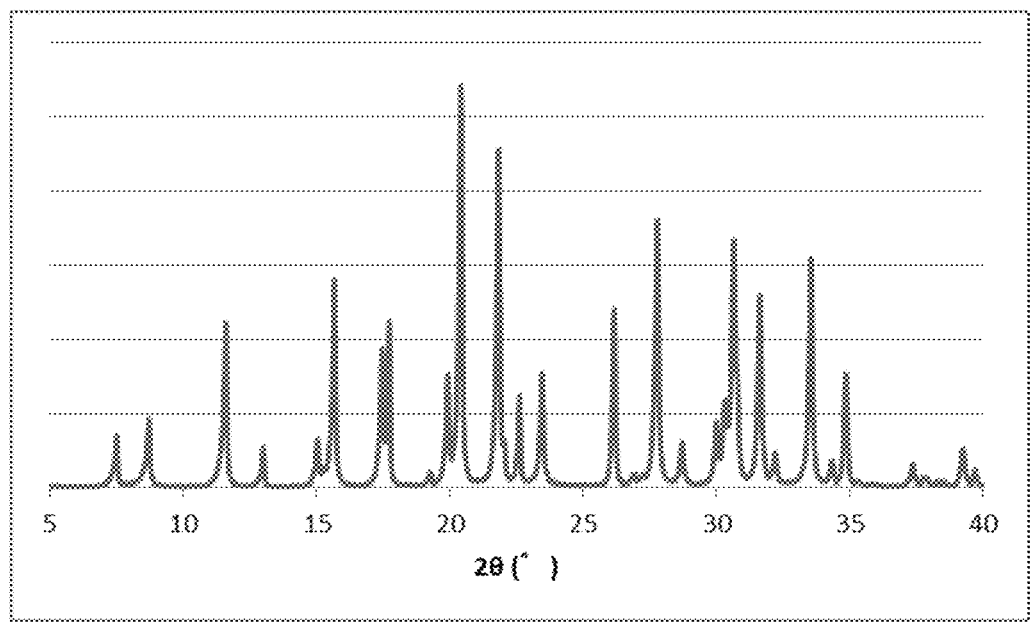

COMPOUND, AND METHOD FOR PRODUCING THE SAME

TECHNICAL FIELD

The present invention relates to a novel compound and a method for producing the same. More particularly, the present invention relates to N,N'-dialkylbicyclo[2.2.2]octane-2,3:5,6-dipyrrolidine and a method for producing the same.

BACKGROUND ART

N,N,N',N'-tetraalkylbicyclo[2.2.2]oct-7-ene-2,3:5,6-dipyrrolidinium is a useful compound that is used as a raw material of a porous crystalline material (e.g., Organic Structure-Directing Agent (OSDA)) such as zeolite (see, for example, Patent Literatures 1 to 3).

For example, for preparing N,N,N',N'-tetraethylbicyclo [2.2.2]oct-7-ene-2,3:5,6-dipyrrolidinium (I), bicyclo[2.2.2] oct-7-ene-2,3:5,6-tetracarboxylic dianhydride (II) as a starting material is first reacted with ethylamine to obtain N,N'-diethylbicyclo[2.2.2]oct-7-ene-2,3:5,6-tetracarboxydiimide (III), as shown below. Subsequently, the resulting imide compound (III) is reduced using lithium aluminum hydride (LiAlH$_4$) to obtain N,N'-diethylbicyclo[2.2.2]oct-7-ene-2,3:5,6-dipyrrolidine (IV). From the dipyrrolidine compound (IV), N,N,N',N'-teraethylbicyclo[2.2.2]oct-7-ene-2,3:5,6-dipyrrolidinium (I) is derived.

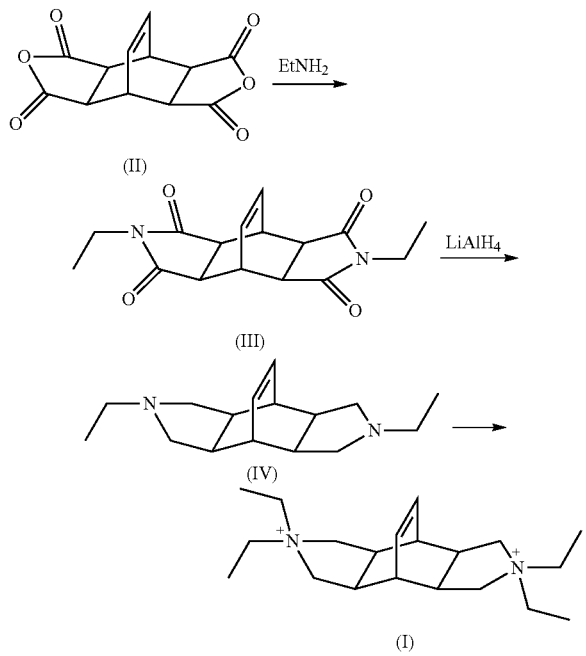

CITATION LIST

Patent Literature

Patent Literature 1: U.S. Unexamined Patent Application Publication No. 6049018
Patent Literature 2: Japanese Patent Laid-Open No. 2016-169139
Patent Literature 3: U.S. Unexamined Patent Application Publication No. 6656268

SUMMARY OF INVENTION

Technical Problem

In the synthesis of N,N'-diethylbicyclo[2.2.2]oct-7-ene-2, 3:5,6-dipyrrolidine (also referred to as precursor hereinafter), a reducing agent having high reactivity needs to be used in order to reduce a carbonyl group in the imide compound (III). However, the reducing agent having high reactivity has a risk of ignition or the like and is difficult to handle. On that account, it is difficult to industrially mass-produce the precursor from the viewpoints of difficulty in control of the reaction and safety issues. Under such circumstances, a compound useful for producing OSDA, which can be safely and easily synthesized, has been desired.

The present invention has been made in the light of the above circumstances, and it is an object of the present invention to provide a novel compound that can be industrially safely and easily produced and is useful for producing OSDA, and a method for producing the compound.

In addition to the object referred to herein, exertion of working-effect that is derived from each constitution shown in Description of Embodiments described later and is not obtained by the conventional techniques can be also positioned as another object of the present invention.

Solution to Problem

The present inventors have intensively studied provision of a compound that is useful for producing OSDA, and as a result and have found that a prescribed compound having a bicyclo[2.2.2]octane-2,3:5,6-dipyrrolidine skeleton can be safely and easily synthesized, and they have completed the present invention.

That is to say, the present invention provides various specific embodiments shown below.

[1]
A method for producing a compound represented by formula (2), comprising at least
   a step of preparing a compound represented by formula (1); and
   a step of reacting the compound represented by formula (1) with a hydrogen source using a catalyst,

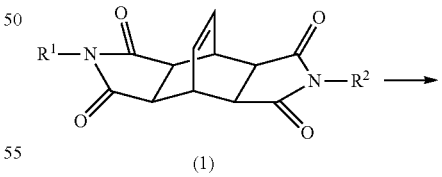

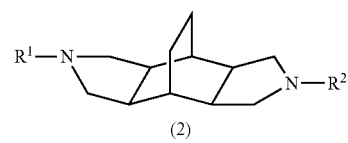

wherein R$^1$ and R$^2$ are each independently an alkyl group.

[2]
The method according to [1], wherein R$^1$ and R$^2$ in formula (1) and formula (2) are each an ethyl group.

[3]

The method according to [1] or [2], wherein the hydrogen source comprises one or more selected from molecular hydrogen, ammonium formate, sodium formate, hydrazine and sodium boron hydride.

[4]

The method according to [1] or [2], wherein the hydrogen source is molecular hydrogen.

[5]

The method according to any one of [1] to [4], wherein the reaction step is carried out by a wet process.

[6]

The method according to any one of [1] to [5], wherein the catalyst is a heterogeneous catalyst.

[7]

A compound represented by formula (2):

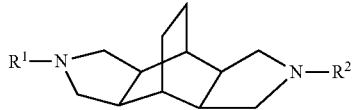

(2)

wherein $R^1$ and $R^2$ are each independently an alkyl group.

[8]

The compound according to [7], wherein $R^1$ and $R^2$ in formula (2) are each an ethyl group.

Advantageous Effects of Invention

The compound of the present invention can be simply and safely synthesized from N,N'-dialkylbicyclo[2.2.2]oct-7-ene-2,3:5,6-tetracarboxydiimide, and is industrially advantageous. Moreover, the compound of the present invention is useful as a precursor or an intermediate of a compound (OSDA) that becomes a raw material of a porous crystalline material such as zeolite.

BRIEF DESCRIPTION OF DRAWING

FIG. 1 is a view showing XRD data of AFX-type zeolite obtained in Reference Example 1.

DESCRIPTION OF EMBODIMENTS

The embodiments of the present invention will be described in detail with reference to the drawing. The following embodiments are examples (typical examples) of embodiments of the present invention, and the present invention is not limited thereto. That is to say, the present invention can be arbitrarily changed and carried out within the scope without departing from the spirit of the present invention. Herein, when an expression using "to" with numerical values or property values before and after that is made, the expression is used to include the values before and after that. For example, the expression of a numerical value range "1 to 100" includes both the upper limit "100" and the lower limit "1". The same shall apply to expressions of other numerical value ranges.

(Compound)

The compound of the present embodiment is a compound represented by formula (2). The compound of the present embodiment has a bicyclo[2.2.2]octane-2,3:5,6-dipyrrolidine skeleton similarly to N,N,N',N'-tetraalkylbicyclo[2.2.2]oct-7-ene-2,3:5,6-dipyrrolidinium for use as a raw material of OSDA, and is useful as a precursor or an intermediate of a raw material of OSDA. As described in a preferred production method described later, the compound of the present embodiment can be simply and safely synthesized without using a reducing reagent which is difficult to handle and reaction control of which is difficult, such as $LiAlH_4$, and therefore, this compound is industrially advantageous.

Herein, the compound represented by formula (2) is also referred to as N,N'-dialkylbicyclo[2.2.2]octane-2,3:5,6-dipyrrolidine

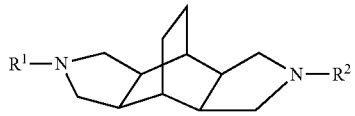

(2)

In formula (2), $R^1$ and $R^2$ are each independently an alkyl group. The alkyl group is preferably a linear or branched alkyl group having 1 to 4 carbon atoms, and specific examples thereof include a methyl group, an ethyl group, an n-propyl group, an isopropyl group, an n-butyl group, an isobutyl group, a sec-butyl group and a tert-butyl group.

Among these alkyl groups, a methyl group, an ethyl group, an n-propyl group and an isopropyl group are preferable, and a methyl group and an ethyl group are more preferable, and an ethyl group is still more preferable.

Specific examples of the compounds represented by formula (2) include the following compounds.

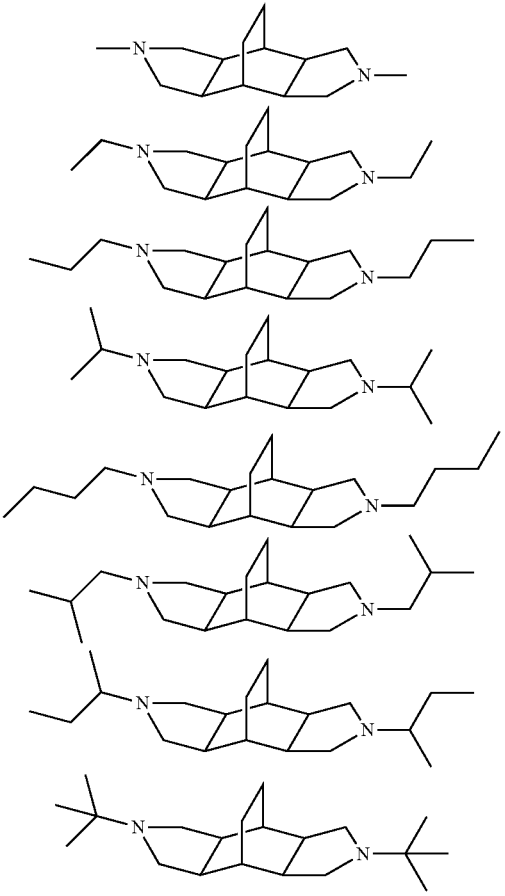

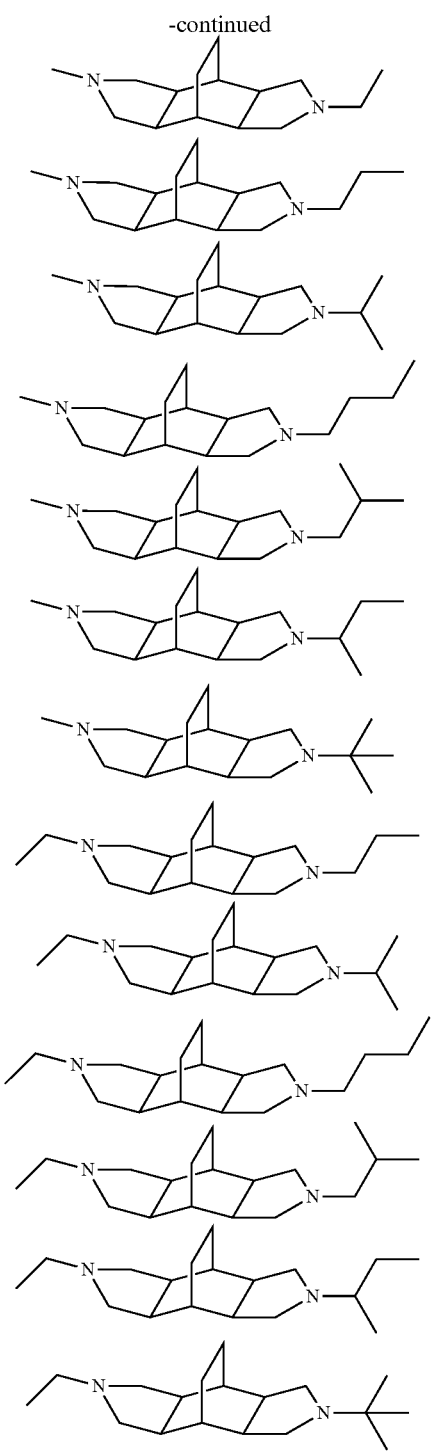

(Production Method)

The compound represented by formula (2) of the present embodiment can be produced through a known synthetic route, and the production method therefor is not particularly limited. Especially, like the conventional techniques described above, a production method without using a reducing reagent which is difficult to handle and reaction control of which is difficult, such as LiAlH$_4$, is preferable from the industrial viewpoint. Specifically, a production method comprising a step of reacting the compound represented by formula (1) with a hydrogen source using a catalyst is particularly preferable. The compound represented by formula (1) is also referred to as N,N'-dialkylbicyclo[2.2.2]oct-7-ene-2,3:5,6-tetracarboxydiimide.

A particularly preferred production method of the present embodiment can be represented by the following scheme.

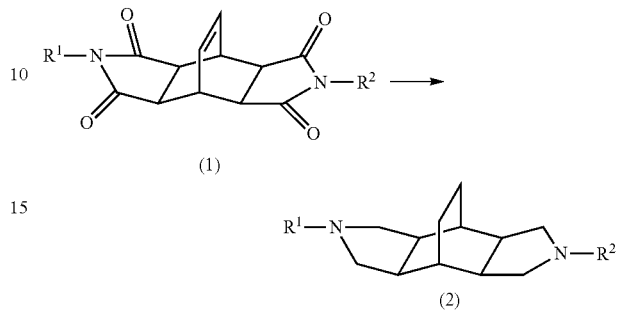

In this production method, there is no need to use a strong reducing agent that is difficult to handle, such as a reducing agent having a risk of ignition or the like, and therefore, N,N'-dialkylbicyclo[2.2.2]oct-7-ene-2,3:5,6-tetracarboxydiimide can be safely and easily produced. According to this production method, since the compound can be synthesized under relatively safe conditions, the facility burden is small, and production in large lots is feasible, so that productivity and economic efficiency of the resulting compound represented by formula (2) are enhanced.

$R^1$ and $R^2$ in the compound represented by formula (1) in the above scheme have the same meanings as those of $R^1$ and $R^2$ in formula (2), and examples of preferred substituents thereof include the same groups as those of $R^1$ and $R^2$ in formula (2).

The compound represented by formula (1) may be obtained as a commercial product, or can be appropriately synthesized through a known synthetic route. For example, the compound may be obtained by synthesizing it through a reaction of a commercially available bicyclo[2.2.2]oct-7-ene-2,3:5,6-tetracarboxylic dianhydride with an alkylamine or its salt.

The hydrogen source for use in the above production method can be appropriately selected from substances capable of hydrogenating the compound represented by formula (1), and the selected one can be used. Specific examples include, but are not limited to, molecular hydrogen such as hydrogen gas; and hydrogen donors, such as ammonium formate, sodium formate, hydrazine and sodium boron hydride (SBH). These hydrogen sources may be used singly or may be used in combination of two or more thereof. Among these hydrogen sources, molecular hydrogen is preferable.

As the catalyst for use in the above production method, a catalyst that can be usually used for hydrogenation can be used, and its type is not particularly limited. The catalyst is preferably a heterogeneous catalyst. By using a heterogeneous catalyst, operations of post treatment, etc. are simple, and even if the compound is produced in large lots, productivity and economic efficiency of the compound are enhanced.

The catalyst is preferably a catalyst containing a transition metal.

Examples of the transition metals include metals such as palladium (Pd), platinum (Pt), rhodium (Rh), vanadium (V), iron (Fe), cobalt (Co), nickel (Ni), copper (Cu), ruthenium (Ru), rhenium (Re), osmium (Os), molybdenum (Mo) and tungsten (W). These metals may be used singly or may be used in combination of two or more thereof.

The above-mentioned transition metals may be each supported on a carrier. The carrier is not particularly restricted as long as it is a carrier usually used as a carrier of a catalyst. Examples thereof include inorganic oxides, activated carbon, and ion-exchange resins. Specific examples of the inorganic oxides include silica ($SiO_2$), titania ($TiO_2$), zirconia ($ZrO_2$), alumina ($Al_2O_3$), magnesium oxide (MgO), tricalcium phosphate (HAP; hydroxy apatite), and composites of two or more of these inorganic oxides (e.g., zeolite).

As the catalyst for use in the above production method, a catalyst in which Pt and V are supported on a carrier can be preferably used. By using the catalyst in which Pt and V are supported on a carrier, the compound represented by formula (2) can be reduced under milder conditions.

Herein, the catalyst in which Pt and V are supported on a carrier is also expressed as "Pt-V/Z". Here, Z represents a carrier.

Platinum to constitute the Pt-V/Z is preferably, for example, platinum particles though it is not particularly limited. Here, the platinum particles are particles of at least one type of metallic platinum and platinum oxide, and are preferably particles of metallic platinum.

The platinum particles are not particularly limited as long as they contain at least platinum, and may contain noble metals such as ruthenium, rhodium and palladium in small amounts.

The platinum particles may be primary particles or may be secondary particles. The average particle diameter of the platinum particles is preferably 1 to 30 nm, and more preferably 1 to 10 nm. The average particle diameter refers to an average value of diameters of any number of particles observed by an electron microscope.

Vanadium to constitute the Pt-V/Z is preferably, for example, vanadium oxide though it is not particularly limited. Examples of the vanadium oxides include vanadic acid ion ($VO_4^{3-}$, $VO_3^{3-}$), vanadium pentoxide, vanadium(II) oxide, and vanadium(IV) oxide. Among these vanadium oxides, $V_2O_5$ is preferable.

The compositional ratio between Pt and V in the Pt-V/Z is preferably 1:0.001 to 10, and more preferably 1:0.005 to 5, in terms of Pt as a metal:V as a metal by number of moles.

The carrier Z in the Pt-V/Z is not particularly limited, but the adsorption capacity of the carrier may be 0.1 to 300 m$^2$/g in terms of BET value, and the average particle diameter thereof may be 0.02 to 200 μm.

Examples of shapes of the carrier include, but are not limited to, powder shape, spherical particle shape, amorphous granule shape, cylindrical pellet shape, extrusion shape, and ring shape.

The component to constitute the carrier is preferably HAP among the aforesaid carriers.

The Pt-V/Z can be produced by mixing a mixed liquid of a platinum compound and a vanadium compound with a carrier to obtain a mixture and drying the mixture.

Examples of the platinum compounds include platinum complex salts, such as platinum acetylacetonate (Pt(acac)$_2$), tetraamminepIatinum(II) acetate, dinitrodiamminepIatinum (II), hexaammineplatinum(IV) carbonate and bis(dibenzalacetone)platinum(0), and salts, such as platinum chloride and potassium tetrachloroplatinate. Among these platinum compounds, Pt(acac)$_2$ is preferable.

Examples of the vanadium compounds include vanadium complex salts, such as vanadyl acetylacetonate (VO(acac)$_2$) and tetramethylammonium bis(tartrato)bis[oxovanadate (IV)], and salts, such as ammonium vanadate(V) and vanadium naphthenate. Among these vanadium compounds, VO(acac)$_2$ is preferable.

The mixed liquid in the production of the Pt-V/Z is a liquid in which the platinum compound and the vanadium compound are suspended or dissolved in a solvent. Examples of the solvents include water, and organic solvents such as alcohol and acetone. The solvents may be used singly or in combination of two or more thereof.

The mixed liquid is mixed with the carrier. The method of mixing the mixed liquid and the carrier is not particularly limited, and the components only need to be sufficiently dispersed. The amount of the carrier is preferably 0.1 to 100 g, and more preferably 1 to 10 g, based on 0.1 mmol of platinum in terms of metal. After the carrier is mixed, the mixture is preferably stirred for 0.5 to 12 hours.

From the mixture of the mixed liquid and the carrier, the solvent is removed by a rotary evaporator or the like, and thereafter, the mixture is dried. Drying is preferably carried out, for example, at 80 to 200° C. for 1 to 60 hours. After the drying, it is preferable to pulverize the dried product as needed and to calcine the product using a muffle furnace or the like.

The above production method is specifically, for example, a method in which the compound represented by formula (1) is provided, and the compound is mixed with the catalyst and the hydrogen source to react with each other.

Here, the compound represented by formula (1), the catalyst and the hydrogen source may be mixed in any order. In the production method of the present embodiment, it is preferable that the compound represented by formula (1) and the catalyst be mixed, then the solvent be added as needed, and thereafter, the hydrogen source be introduced into the reactor, from the viewpoint of workability.

In the production method of the present embodiment, molecular sieves may be added to the reaction system in order to promote the reaction under the conditions at a low temperature and a low pressure. The amount of the molecular sieves to be added is preferably 0.1 to 10 times, more preferably 0.5 to 5 times, the mass of the compound represented by formula (1).

The reaction in the present embodiment may be carried out in the presence of a solvent, that is, by a wet process.

The solvent is not particularly restricted as long as it can dissolve the compound represented by formula (1), and can be appropriately selected according to the reaction temperature, the reactant, etc.

Examples of the solvents include water; aromatic hydrocarbon-based solvents, such as benzene and toluene; amide-based solvents, such as acetonitrile, N,N-dimethylacetamide and N,N-dimethylformamide; ether-based solvents, such as tetrahydrofuran (also referred to as THF hereinafter), diethyl ether and 1,2-dimethoxyethane; alcohol-based solvents, such as methanol, ethanol and isopropanol; and halogen-based solvents, such as dichloromethane, dichloroethane and chloroform. These solvents can be used singly or in any combination and ratio of two or more thereof.

Among these solvents, ether-based solvents are preferable, and 1,2-dimethoxyethane is more preferable.

Whether to use the solvent or not and the amount of the solvent to be used can be appropriately determined taking other reaction conditions into consideration and are not particularly restricted, but the concentration of the compound represented by formula (1) in the reaction mixture is preferably set to 0.001 to 10 mol/L, more preferably 0.01 to 5 mol/L, and still more preferably 0.01 to 3 mol/L.

The amount of the catalyst to be used is preferably set to 0.1 to 50 times, more preferably 0.5 to 20 times, still more preferably 1 to 10 times, the mass of the compound represented by formula (1).

The reaction temperature is usually in the range of 10 to 200° C., preferably 50 to 150° C., and more preferably 50 to 120° C., though it is not particularly restricted.

The reaction time can be appropriately adjusted by monitoring the progress of the reaction using GC-MS or the like, and it is usually 1 minute to 100 hours, preferably 0.5 hour to 70 hours, and more preferably 1 hour to 60 hours.

When molecular hydrogen is used in the production method of the present embodiment, the hydrogen pressure in the reactor is usually 0.1 to 10 MPa, preferably 1.0 to 10 MPa, and more preferably 2.0 to 8.0 MPa.

With regard to the mixture after completion of the reaction, when a solvent is used in the reaction, the resulting reaction solution is concentrated as needed, and then the residue may be used, as it is, as a raw material or a precursor or an intermediate, or the reaction mixture may be appropriately subjected to post treatment to obtain a compound represented by the aforesaid formula (2). Specific examples of the post treatments include known purification methods, such as washing with water, filtration, drying, extraction, distillation and chromatography. These purification methods may be carried out in combination of two or more thereof.

EXAMPLES

The features of the present invention will be more specifically described with reference to examples and comparative examples hereinafter, but the present invention is in no way limited to those examples. That is to say, the materials, the amounts used, the ratios, the processing details, the processing procedure, etc. shown in the following examples can be appropriately changed without departing from the spirit of the present invention. Moreover, various production conditions and the values of evaluation results in the following examples mean preferred upper limits or preferred lower limits in the embodiments of the present invention, and a preferred range may be a range defined by a combination of any value of the above-mentioned upper limits or lower limits and any value of the following examples or a combination of values of the following examples.

Production Example 1: Preparation of Pt-V/HAP Catalyst

To 90 mL of acetone, Pt(acac)$_2$ (platinum acetylacetonate, 0.4 mmol) manufactured by N.E. CHEMCAT Corporation and VO(acac)$_2$ (vanadyl acetylacetonate, 0.4 mmol) from Sigma-Aldrich Co. LLC were added, and they were stirred for 30 minutes at room temperature. Further, 1.0 g of HAP (trade name "Tricalcium Phosphate") from Wako Pure Chemical Industries, Ltd. was added, followed by stirring for 4 hours at room temperature. From the resulting mixture, the solvent was removed by a rotary evaporator to obtain a light green powder. The resulting powder was dried at 110° C. all night. The dried powder was pulverized in an agate mortar and calcined at 300° C. for 3 hours in the atmosphere to obtain a dark gray powder (Pt-V/HAP).

Production Example 2: Synthesis of N,N'-diethylbicyclo[2.2.2]oct-7-ene-2,3:5,6-tetracarbonyldiimide In a 2 L flask, 4.0 g of bicyclo[2.2.2]oct-7-ene-2,3:5,6-tetracarboxylic dianhydride (molecular weight: 248.19, powder, manufactured by Tokyo Chemical Industry Co., Ltd.) and 25 mL of a 70° ethylamine solution (molecular weight: 81.54, solid, manufactured by Tokyo Chemical Industry Co., Ltd.) were placed, then 12 mL of water was added, they were stirred using a stirrer on a hot stirrer, and atmosphere was set to a nitrogen atmosphere. Stirring was carried out at room temperature. The temperature was raised up to 60° C., then gradually raised and finally set to 100° C. After the reaction was carried out for 44 hours, the reaction mixture was allowed to cool, then filtered, washed with pure water and dried, to obtain 1.6 g of a white solid of N,N'-diethylbicyclo[2.2.2]oct-7-ene-2,3:5,6-tetracarboxydiimide (yield: 95% or more).

$^1$H-NMR and $^{13}$C-NMR of the resulting white solid are shown below.

$^1$H-NMR (400 MHz, CDCl$_3$) δ: 6.10 (t, 2H), 3.79 (brs, 2H), 3.48 (q4, 4H), 2.96 (s, 4H), 1.07 (t, 6H).

$^{13}$C-NMR (400 Hz, CDCl$_3$) δ: 176.47 (×4), 130.75 (×2), 42.83 (×4), 33.84 (×2), 33.47 (×2), 12.90 (×2).

Example 1: Synthesis of N,N'-diethylbicyclo[2.2.2]octane-2,3:5,6-dipyrrolidine To a 50 mL stainless steel autoclave, 0.3 g of Pt-V/HAP obtained in Production Example 1, 0.3 mmol of N,N'-diethylbicyclo[2.2.2]oct-7-ene-2,3:5,6-tetracarbonyldiimide obtained in Production Example 2, and 0.1 g of molecular sieves 4 Å from Wako Pure Chemical Industries, Ltd. were added. Further, 5 mL of 1,2-dimethoxyethane (DME) was added as a solvent. Hydrogenation reaction was carried out at a reaction temperature of 150° C. and a hydrogen pressure of 5 MPa for 48 hours to obtain N,N'-diethylbicyclo[2.2.2]octane-2,3:5,6-dipyrrolidine. After the reaction, the yield of N,N'-diethylbicyclo[2.2.2]octane-2,3:5,6-dipyrrolidine measured using GC-MS was 77%.

The product was isolated, and the measurement results of $^1$H-NMR and $^{13}$C-NMR are shown below.

$^1$H NMR (400 MHz, CDCl$_3$) δ=2.72 (t, J=17 Hz, 4H), 2.49 (dd, J=30, 14 Hz, 4H), 2.43 (dd, J=18, 10 Hz, 4H), 2.21 (s, 4H), 1.57 (s, 4H), 1.40 (s, 2H), 1.14 (t, J=15 Hz, 6H);

$^{13}$C NMR (100 MHz, CDCl$_3$) δ=57.0 (×4), 50.2 (×2), 40.7 (×4), 30.6 (×2), 14.6 (×2), 13.9 (×2).

Production Example 3: Preparation of Rh-Mo/HAP

To a 100 mL eggplant type flask containing 80 mL of distilled water, 0.2 mmol of K$_3$[RhCl$_6$] manufactured by N.E. CHEMCAT Corporation was added, and ultrasonic treatment was carried out for 3 minutes. Thereafter, 1.0 g of HAP (trade name "Tricalcium Phosphate") from Wako Pure Chemical Industries, Ltd. was added while strongly stirring, the resulting solution was heated up to 80° C. and stirred for 15 hours in this state, and thereafter, the solution was allowed to stand still for 1.5 hours to allow it to cool down to room temperature. To the solution having been allowed to cool, 25 mL of (NH$_4$)$_6$Mo$_7$O$_{24}$·4H$_2$Oaq (40 mM) (Mo content: 1.0 mmol) was dropwise added, and thereafter, the solution was heated up to 50° C. and stirred for 3 hours. After the stirring, the solution was filtered and subjected to filtration and washing using about 1 L of distilled water. The residue obtained after the filtration and washing was dried at 120° C. for 8 hours or longer to obtain Rh-Mo/HAP (Rh: 0.2 mmol/g, Mo: 0.017 mmol/g).

To an autoclave to be used for reaction, the catalyst obtained in Production Example 3 and 5 mL of DME (1,2-dimethoxyethane) that was a solvent were added, then the solution was pressurized to 20 atm with hydrogen gas, heated to 160° C. and subjected to reduction treatment for 1 hour. Thereafter, the solution was centrifuged (2000 rpm, 1 minute), and the supernatant liquid was removed with a pipette. Thereto was added 5 mL of DME, and ultrasonic treatment was carried out for 1 minute. After this washing step was repeated again, the supernatant liquid was removed for the last time to achieve pre-reaction reduction treatment.

Example 2: Synthesis of N,N'-diethylbicyclo[2.2.2]octane-2,3:5,6-dipyrrolidine

N,N'-diethylbicyclo[2.2.2]octane-2,3:5,6-dipyrrolidine was obtained in the same manner as in Example 1, except that 0.3 g of Rh-Mo/HAP obtained in Production Example 3 was used instead of Pt-V/HAP, and the temperature was changed to 160° C. After the reaction, the yield of N,N'-diethylbicyclo[2.2.2]octane-2,3:5,6-dipyrrolidine measured using GC-MS was 60%.

Reference Example 1: Synthesis of AFX-Type Zeolite

Synthesis of N,N,N',N'-tetraethylbicyclo[2.2.2]octane-2,3:5,6-dipyrrolidinium diiodide In the same manner as in Example 1, 2.2 g of N,N'-diethylbicyclo[2.2.2]octane-2,3:5,6-dipyrrolidine (molecular weight: 248.41) was synthesized, then a 50 mL ethanol solution thereof was placed in a 100 mL flask, and 6.0 g of ethyl iodide (molecular weight: 155.97, liquid, Tokyo Chemical Industry Co., Ltd.) was dropwise added. The resulting solution was refluxed for 2 days in a nitrogen atmosphere, then allowed to cool, then filtered, washed with acetone and dried to obtain 2.6 g of a white powder of N,N,N',N'-tetraethylbicyclo[2.2.2]octane-2,3:5,6-dipyrrolidinium diiodide that was a desired product (yield, 52%). $^1$H-NMR and $^{13}$C-NMR of the resulting white powder are shown below.

$^1$H-NMR (400 MHz, D$_2$O) δ: 3.82 (dd, 4H), 3.49 (q4, 4H), 3.38 (q4, 4H), 3.33 (d, 4H), 2.68 (m, 4H), 1.80 (s, 2H), 1.64 (s, 4H), 1.36 (t, 6H), 1.31 (t, 6H)

$^{13}$C-NMR (400 Hz, CDCl$_3$) δ: 65.00 (×4), 58.51 (×2), 54.41 (×2), 40.11 (×4), 28.33 (×2), 14.86 (×2), 11.01 (×2), 10.1 (×2)

(Synthesis of AFX-Type Zeolite)

In a SUS beaker, 2.0 g of N,N,N',N'-tetraethylbicyclo[2.2.2]octane-2,3:5,6-dipyrrolidinium diiodide (molecular weight: 558.62), 8.4 g of a 4.8 mass % sodium hydroxide solution, 2.7 g of FAU-type zeolite CBV712 (manufactured by Zeolyst International Inc., silica-to-alumina ratio SAR 10.9) and 3.3 g of water were stirred for 48 hours. The composition of the mixture was as follows.

TABLE 1

| SiO$_2$ | |
|---|---|
| 0.092 | Al$_2$O$_3$ |
| 0.106 | OSDA |
| 0.153 | Na$_2$O |
| 19.98 | H$_2$O |

The numerical value of each component in the mixture means a ratio of an amount of substance with the proviso that the amount of substance of SiO$_2$ is 1.

Subsequently, this raw material composition (mixture) was placed in a stainless-steel pressure-tight, sealed container with a 50 cc inner cylinder of Teflon®, and allowed to stand still for 48 hours at 170° C. The product after this hydrothermal treatment was subjected to solid-liquid separation, and the resulting solid phase was washed with a sufficient amount of water and dried at 105° C. to obtain a product. Powder X-ray diffraction analysis confirmed that the product is a single phase AFX-type zeolite.

In FIG. 1, XRD data of the AFX-type zeolite are shown.

INDUSTRIAL APPLICABILITY

According to the present invention, N,N'-diethylbicyclo[2.2.2]octane-2,3:5,6-dipyrrolidine that is useful as an intermediate raw material or the like of a compound that becomes a material of OSDA can be simply and safely provided, and for example, supply of zeolite that is a kind of hydrous aluminosilicate can be achieved relatively stably and at low cost. On that account, the present invention can be widely and effectively utilized for applications in not only various adsorbents or separating agents of inorganic or organic molecules but also desiccants, dehydrating agents, ion exchangers, petroleum refining catalysts, petrochemical catalysts, solid acid catalysts, three-way catalysts, exhaust gas cleaning catalysts, NOx occlusion materials, etc.

The invention claimed is:

1. A method for producing a compound of formula (2), the method comprising:

reacting a compound of formula (1) with a hydrogen source in the presence of a catalyst,

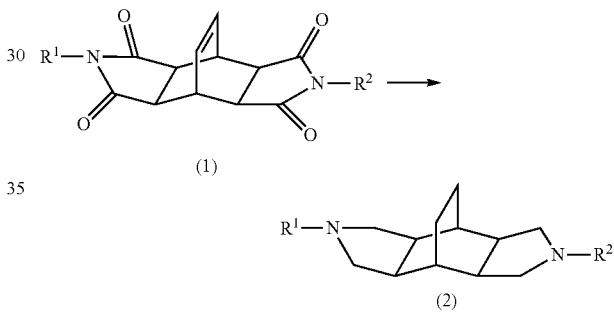

wherein R$^1$ and R$^2$ are each independently an alkyl group.

2. The method according to claim 1, wherein R$^1$ and R$^2$ are each an ethyl group.

3. The method according to claim 1, wherein the hydrogen source comprises one or more selected from the group consisting of molecular hydrogen, ammonium formate, sodium formate, hydrazine and sodium boron hydride.

4. The method according to claim 1, wherein the hydrogen source is molecular hydrogen.

5. The method according to claim 1, wherein the reacting is carried out by a wet process.

6. The method according to claim 1, wherein the catalyst is a heterogeneous catalyst.

7. A compound of formula (2):

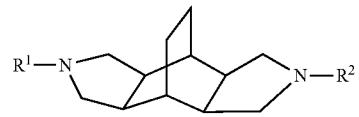

wherein R$^1$ and R$^2$ are each an ethyl group.

* * * * *